(12) United States Patent
Johnson et al.

(10) Patent No.: US 11,260,204 B2
(45) Date of Patent: Mar. 1, 2022

(54) SPRING RETRACT IV CATHETER

(71) Applicant: Smiths Medical ASD, Inc., Plymouth, MN (US)

(72) Inventors: Daniel Casey Johnson, Minneapolis, MN (US); Eric Jason Krause, Big Lake, MN (US); David J. Goral, Brookfield, CT (US); Jay T. Breindel, Branford, CT (US); Tye Jensen, Golden Valley, MN (US); Marco Monti, Latina (IT)

(73) Assignee: Smiths Medical ASD, Inc., Plymouth, MN (US)

( * ) Notice: Subject to any disclaimer, the term of this patent is extended or adjusted under 35 U.S.C. 154(b) by 80 days.

(21) Appl. No.: 16/378,765

(22) Filed: Apr. 9, 2019

(65) Prior Publication Data
US 2019/0314615 A1 Oct. 17, 2019

Related U.S. Application Data

(60) Provisional application No. 62/656,195, filed on Apr. 11, 2018.

(51) Int. Cl.
*A61M 25/06* (2006.01)
*A61M 25/00* (2006.01)
*A61M 5/32* (2006.01)

(52) U.S. Cl.
CPC .... *A61M 25/0631* (2013.01); *A61M 25/0606* (2013.01); *A61M 5/322* (2013.01); *A61M 25/0097* (2013.01)

(58) Field of Classification Search
CPC .......... A61M 25/0606; A61M 25/0631; A61M 25/0612; A61M 25/0618; A61M 5/3234;
(Continued)

(56) References Cited

U.S. PATENT DOCUMENTS

| 5,195,983 | A |   | 3/1993 | Boese |
| 6,056,726 | A | * | 5/2000 | Isaacson ........... A61M 25/0631 |
|           |   |   |        | 604/164.01 |

(Continued)

FOREIGN PATENT DOCUMENTS

| WO | WO 2004/050138 A2 | 6/2004 |
| WO | WO 2017/029374 A1 | 2/2017 |

(Continued)

OTHER PUBLICATIONS

Search Report and Written Opinion dated Jul. 22, 2019 for PCT Application No. PCT/US2019/026469, 16 pages.

(Continued)

*Primary Examiner* — Deanna K Hall
(74) *Attorney, Agent, or Firm* — Patterson Thuente Pedersen, P.A.

(57) ABSTRACT

A safety catheter insertion device configured to automatically retract a needle cannula following insertion of a catheter assembly and to inhibit release of the catheter assembly from the safety catheter insertion device until the needle cannula has been retracted for the purpose of inhibiting inadvertent needle sticks. The safety catheter insertion device including an advancement arm slidably coupled to a needle housing assembly and configured to shift between a first position in which a needle cannula traverses through a catheter hub coupling portion of the advancement arm to inhibit release of a catheter assembly, and a second position in which one or more tabs of the advancement arm interact with one or more retention arms of the needle housing assembly to enable a biasing mechanism to shift the needle assembly to a proximal position and enable release of the catheter assembly from the safety catheter insertion device.

15 Claims, 11 Drawing Sheets

(58) Field of Classification Search
CPC .......... A61M 2005/3206; A61M 5/322; A61M 25/0097; A61M 25/0693; A61M 2005/3267; A61M 5/3275
See application file for complete search history.

(56) References Cited

U.S. PATENT DOCUMENTS

| | | | |
|---|---|---|---|
| 6,582,402 B1* | 6/2003 | Erskine | A61M 5/3269 604/164.08 |
| 7,604,616 B2 | 10/2009 | Thoresen et al. | |
| D808,013 S | 1/2018 | Chheda et al. | |
| 10,028,691 B2 | 7/2018 | Goral et al. | |
| D844,774 S | 4/2019 | Akcay et al. | |
| D893,711 S | 8/2020 | Chheda et al. | |
| 2005/0182363 A1 | 8/2005 | Kulli | |
| 2007/0083167 A1 | 4/2007 | Smiths et al. | |
| 2007/0260185 A1* | 11/2007 | Popov | A61M 25/0612 604/164.08 |
| 2009/0088696 A1 | 4/2009 | Harding et al. | |
| 2010/0191189 A1* | 7/2010 | Harding | A61M 25/0625 604/164.08 |
| 2011/0071469 A1* | 3/2011 | Wilson | A61M 25/0631 604/110 |
| 2013/0317426 A1 | 11/2013 | Fiser et al. | |
| 2015/0151085 A1 | 6/2015 | Tan et al. | |
| 2015/0224267 A1 | 8/2015 | Farrell et al. | |
| 2015/0335858 A1 | 11/2015 | Woehr et al. | |
| 2016/0135841 A1 | 5/2016 | Albert et al. | |
| 2016/0158526 A1 | 6/2016 | Woehr | |
| 2016/0220762 A1 | 8/2016 | Goral et al. | |
| 2016/0220791 A1 | 8/2016 | Akcay et al. | |
| 2016/0271369 A1 | 9/2016 | Yeh et al. | |
| 2017/0119977 A1 | 5/2017 | Teoh | |
| 2017/0239443 A1 | 8/2017 | Abitabilo et al. | |
| 2018/0296149 A1 | 10/2018 | Goral et al. | |
| 2019/0314614 A1 | 10/2019 | Krause et al. | |
| 2019/0314615 A1 | 10/2019 | Johnson et al. | |
| 2019/0357892 A1 | 11/2019 | Abitabilo et al. | |
| 2020/0009366 A1 | 1/2020 | Abitabilo | |

FOREIGN PATENT DOCUMENTS

| | | |
|---|---|---|
| WO | WO 2019/079719 A1 | 4/2019 |
| WO | WO 2019/152630 A1 | 8/2019 |

OTHER PUBLICATIONS

Search Report and Written Opinion dated Apr. 29, 2019 for PCT Application No. PCT/US2019/016017, 14 pages.
Search Report and Written Opinion dated Jul. 23, 2019 for PCT Application No. PCT/US2019/026467, 11 pages.

* cited by examiner

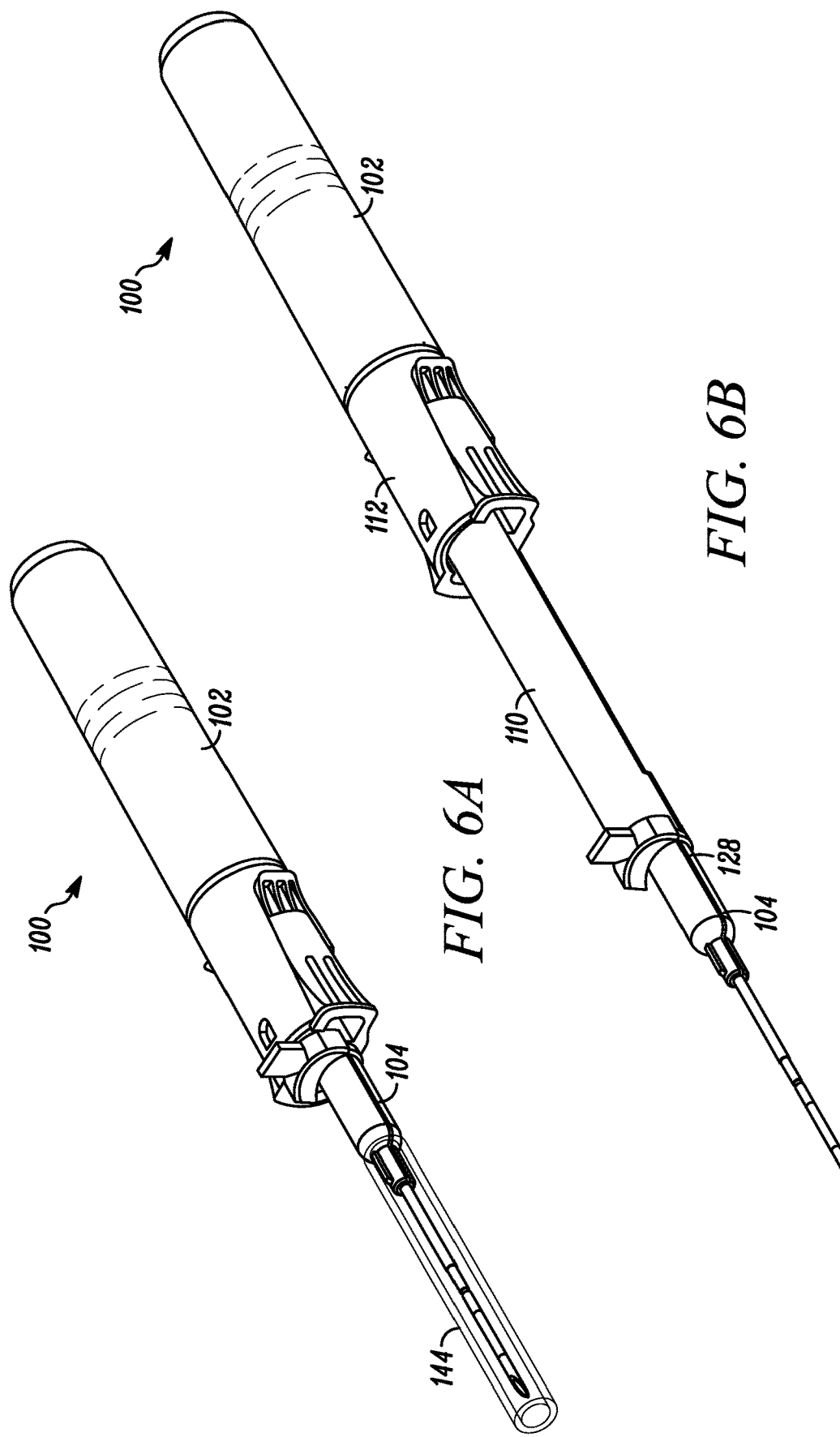

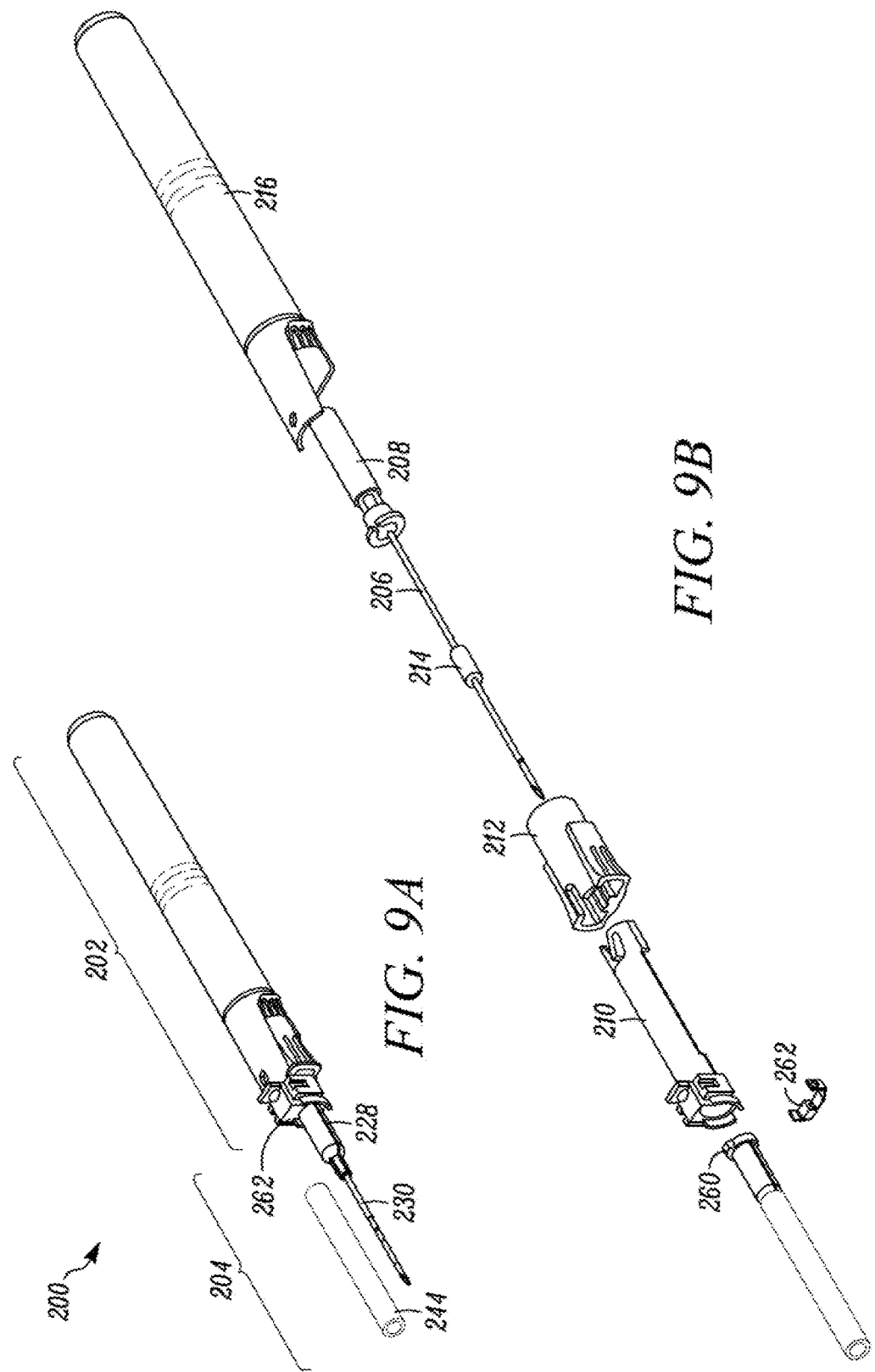

SPRING RETRACT IV CATHETER

RELATED APPLICATION

The present application claims the benefit of U.S. Provisional Application No. 62/656,195 filed Apr. 11, 2018, which is hereby incorporated herein in its entirety by reference.

TECHNICAL FIELD

The present disclosure relates generally to safety catheters, and more particularly to a safety catheter insertion device having a protective needle cannula transposable mechanism for automatic retraction of a used needle cannula into a needle housing to shield a sharp distal tip of the needle cannula prior to release of a catheter hub from the safety catheter insertion device.

BACKGROUND

Intravenous (IV) therapy is a versatile technique used for the administration of medical fluids to and withdrawal of bodily fluids from patients. IV therapy has been used for various purposes, such as the maintenance of blood and electrolyte balance, the transfusion of blood, the administration of nutritional supplements, chemotherapy, and the administration of drugs and medications. These fluids, collectively referred to herein as medicaments, may be administered intravenously by injection through a hypodermic needle, or intermittently or continuously by infusion using a needle or catheter. A common intravenous access device utilized by clinicians is the Peripheral Intravenous Catheter (PIVC).

A PIVC is made of a soft, flexible plastic or silicone, generally between fourteen to twenty-four gauge in size. In the conventional venipuncture procedure, a catheter is inserted into a vein in the patient's hand, foot, or the inner aspect of the arm or any vein in the body that will accept an IV catheter. Typically PIVCs are "over the needle" catheters, where a catheter is coaxially placed over an introducer needle of an intravenous catheter insertion device. In order to properly place the catheter into the patient's vein, the introducer needle is used to puncture the skin, tissue, and vein wall to provide a path for placement of the catheter into the vein.

Placement of the catheter generally includes preparation of a biological site of the patient. Often a tourniquet is applied proximal to the biological site and a variety of techniques can be used to dilate the patient's vein. While wearing disposable gloves, the clinician cleanses the biological site and a vein is retracted or anchored by placing a thumb over the vein about fifty to seventy five mm distal to the site. The introducer needle and catheter are introduced into the vein by inserting a beveled sharpened tip of the introducer needle into the vein at about a twenty to thirty degree angle, with the bevel facing up in order to pierce one wall of the vein. The catheter thus rides with the introducer needle through the skin, tissue, and vein wall into the patient's vein.

Various catheter insertion devices have been developed to provide a needle for catheterization. One such example of this type of catheter insertion device is marketed by Smiths Medical ASD, Inc. of St. Paul, Minn., under the TELCO and INTUITIV trademarks, and are described in U.S. Pat. No. 8,257,322 and U.S. Pat. Publ. Nos. 2011/0319838; and 2017/0095617, the contents of which are incorporated by reference herein. In other cases, the catheter insertion device provides a safety needle assembly that functions to house the sharpened tip of the needle to reduce the likelihood of an inadvertent needle stick. Examples of this type of catheter insertion device are marketed by Smiths Medical ASD, Inc. under the PROTECTIV and VIAVALVE trademarks, and are described in U.S. Pat. Nos. 5,000,740; 7,736,342 and U.S. Pat. Publ. No. 2016/0220791, the contents of which are incorporated by reference herein.

To finish placement, the introducer needle and catheter are lowered towards the skin to decrease the entry angle, and the catheter is advanced slightly into the vein. Once the catheter is satisfactorily positioned within the vein, the introducer needle is typically withdrawn from inside the catheter, and the connection between the catheter and the intravenous catheter device is loosened, so that the catheter can be advanced further into the vein as desired. The catheter can then be secured in place on the biological site by adhesive tape, while the intravenous catheter insertion device is properly disposed of in a sharps container.

It is well-known that an accidental needle stick from an introducer needle that has been in contact with a patient's blood and/or other bodily fluids, presents a risk of the transmission harmful contaminants and/or infectious diseases, including AIDS, hepatitis and other blood-borne illnesses. Because of this threat, attempts have been made to shield the sharpened tip of the introducer needle prior to release of the catheter from the catheter insertion device. However, further improvements could be made to enable a smooth release of the catheter from the catheter insertion device in a way that reduces or eliminates the risk of an inadvertent needle stick. Particularly, some of the safety features of previous attempts require cumbersome or two-handed manipulations to activate. Accordingly, Applicants of the present disclosure have identified a need for an intravenous catheter insertion assembly that addresses these concerns.

SUMMARY OF THE DISCLOSURE

Embodiments of the present disclosure provide a safety catheter insertion device having a protective needle cannula transposable mechanism configured to automatically retract a used needle cannula into a needle housing, such that the sharp distal tip of the needle cannula is shielded prior to release of a catheter hub from the safety catheter insertion device. Moreover, automatic retraction of the needle cannula is passive, in that activation of the transport mechanism occurs naturally during conventional use, and without a need by the user to separately initiate an additional activation procedure. In particular, the needle cannula is automatically retracted as the catheter is advanced into the vein of the patient and the user begins to withdraw the needle cannula from inside the catheter, thereby relieving the user from the cumbersome task of retracting the needle cannula manually. Once retracted, the safety catheter insertion device releases its grip on the catheter hub, thereby ensuring that the sharpened distal tip of the needle cannula is safely housed within the needle housing prior to release of the safety catheter insertion device from the catheter hub.

One embodiment of the present disclosure provides a safety catheter insertion device configured to automatically retract a needle cannula following insertion of a catheter assembly and to inhibit release of the catheter assembly from the safety catheter insertion device until the needle cannula has been automatically retracted for the purpose of inhibiting inadvertent needle sticks. The safety catheter insertion device can include a needle assembly, needle housing, biasing mechanism, and advancement arm. The needle housing assembly can include a needle cannula having a sharpened distal tip and a proximal end operably coupled to a needle hub. The needle housing assembly can be configured to selectively house the sharpened distal tip of the needle assembly in a proximal position. The biasing mechanism can be positioned between the needle hub and the needle housing and configured to bias the needle assembly to the proximal position. The advancement arm can be slidably coupled to the needle housing assembly and can be configured to shift between a first position in which a portion of the needle cannula traverses through a catheter hub coupling portion of the advancement arm to inhibit release of the catheter assembly from the safety catheter insertion device, and a second position in which one or more tabs of the advancement arm interact with one or more retention arms of the needle housing assembly to enable the biasing mechanism to shift the needle assembly to the proximal position to house the sharpened distal tip of the needle assembly in the needle housing assembly and enable release of the catheter assembly from the safety catheter insertion device.

In one embodiment, the needle hub includes one or more tabs, wherein the one or more tabs interlock with the one or more retention arms of the needle housing assembly to retain the needle assembly in a distal position against the bias of the biasing mechanism. In one embodiment the one or more retention arms of the needle housing assembly are constructed of a resilient material in a bias towards engagement with the one or more tabs of the needle hub. In one embodiment the one or more tabs of the advancement arm shift the one or more retention arms of the needle housing assembly against their natural bias away from engagement with the one or more tabs of the needle hub. In one embodiment, in the second position, interaction between one or more retention arms of the needle housing assembly and the one or more tabs of the advancement arm inhibit further shifting of the advancement arm relative to the needle housing assembly.

In one embodiment, the biasing mechanism can be a compression spring. In one embodiment, the catheter hub coupling portion of the advancement arm includes an abutment plate and a hub grip shaped and sized to closely conform to an outer diameter of the catheter hub of the catheter assembly. In one embodiment, the catheter hub coupling portion of the advancement arm includes a hub retention clip. In one embodiment contact between the hub retention clip and a catheter hub of the catheter assembly is maintained by the passage of the needle cannula through a portion of the hub retention clip. In one embodiment, withdrawal of the needle cannula to the proximal position enables a natural bias of the hub retention clip to shift the hub retention clip away from the catheter hub.

Another embodiment of the present disclosure provides the safety catheter insertion device configured to inhibit release of a catheter assembly from a safety catheter insertion device until a needle cannula has been automatically retracted into a needle housing for the purpose of inhibiting inadvertent needle sticks. The safety catheter insertion device can include a needle assembly, needle housing assembly, biasing mechanism, advancement arm, and hub retention clip. The needle assembly can include a needle cannula having a sharpened distal tip and a proximal end operably coupled to the needle hub. The needle housing assembly can be configured to selectively house the sharpened tip of the needle assembly in a proximal position. The biasing mechanism can be positioned between the needle hub and the needle housing and can be configured to bias the needle assembly to the proximal position. The advancement arm can be slidably coupled to the needle housing assembly. The hub retention clip can be operably coupled to a distal portion of the advancement arm. Wherein the advancement arm is configured to slide between a first position, in which a portion of the needle cannula traverses through the hub retention clip to inhibit release of the catheter assembly from the safety catheter insertion device, and a second position, in which the needle cannula is retracted under the bias of the biasing mechanism to the proximal position to house the sharpened distal tip of the needle assembly in the needle housing assembly and to enable release of the catheter assembly from the safety catheter insertion device.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 6A is a perspective view depicting an intravenous catheter insertion assembly in a first ready for use position, in accordance with an embodiment of the disclosure.

FIG. 6B is a perspective view depicting the intravenous catheter assembly of FIG. 6A in a second or safe position, in accordance with an embodiment of the disclosure.

FIG. 9A is a perspective view depicting an intravenous catheter assembly in accordance with an alternative embodiment of the disclosure.

FIG. 9B is a perspective, exploded view depicting the intravenous catheter assembly of FIG. 9A.

Figure 1:
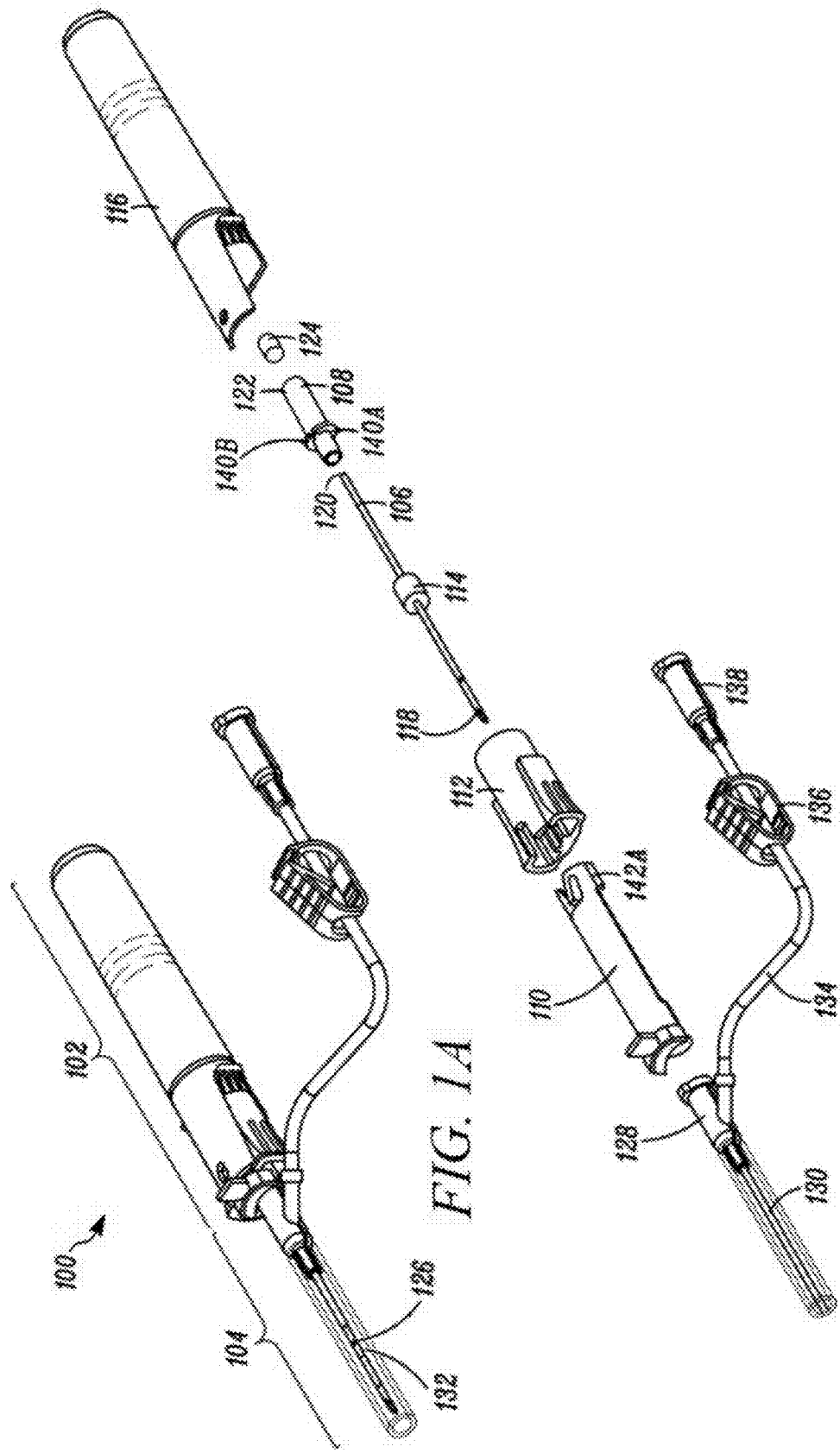
FIG. 1A is a perspective view depicting an intravenous catheter insertion assembly in accordance with an embodiment of the disclosure.
FIG. 1B is a perspective, exploded view depicting the intravenous catheter assembly of FIG. 1A.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Various example embodiments of catheters are described herein for use in accessing the vein of a subject. It is to be appreciated, however, that the example embodiments described herein can alternatively be used to access the vascular of a subject at locations other than a vein, including but not limited to the artery of a subject. It is additionally to be appreciated that the term "clinician" refers to any individual that can perform a catheter insertion procedure with any of the example embodiments described herein or alternative combinations thereof. Similarly, the term "subject," as used herein, is to be understood to refer to an individual or object in which the catheter is to be inserted, whether human, animal, or inanimate. Various descriptions are made herein, for the sake of convenience, with respect to the procedures being performed by a clinician to access the vein of a subject, while the disclosure is not limited in this respect.

It is also to be appreciated that the term "distal," as used herein, refers to the direction along an axis that lies parallel to a needle cannula of a safety catheter assembly that is closest to the subject during catheter insertion. Conversely, the term "proximal," as used herein, refers to the direction lying along the axis parallel to the needle cannula that is further away from the subject when the catheter is inserted into the vein of the subject, opposite to the distal direction.

Referring to FIG. 1A, a perspective view of an intravenous catheter insertion assembly 100 is depicted in accordance with an embodiment of the disclosure. FIG. 1B depicts an exploded view of the intravenous catheter insertion assembly 100 of FIG. 1A. The intravenous catheter insertion assembly 100 can include a safety catheter insertion device 102 and a catheter assembly 104. The safety catheter insertion device 102 can include a needle cannula 106, a needle hub 108, advancement arm 110, handle 112, biasing mechanism 114, and needle housing 116.

The needle cannula 106 can include an elongate cylindrically shaped metal structure defining a lumen that extends between a sharp distal tip 118 and a proximal end 120. The sharp distal needle tip 118 can be constructed and arranged to pierce the skin of a subject during catheter insertion. For example, in one embodiment, the sharp distal tip 118 can include a V-point designed to reduce the penetration force used to penetrate the needle 106 and a portion of the catheter insertion assembly 104 through the skin, tissue, and vein wall of a subject. In one embodiment, the length of the needle cannula 106 can be extended to aid in the insertion of the catheter assembly 104 into obese patients.

The proximal end 120 of the needle cannula 106 can be operably coupled to the needle hub 108. In some embodiments, the needle cannula 106 and needle hub 108 can be collectively referred to as a needle assembly. In one embodiment, the needle hub 108 can be constructed to provide a visual indication of a flashback when the sharpened distal tip 118 of the needle cannula 106 enters the vein of the subject. For example, in one embodiment, the needle hub 108 can define a flash chamber 122 in fluid communication with the lumen of the needle cannula 106. When the sharp distal tip 118 enters a vein during catheter insertion, blood or bodily fluid enters the needle lumen from the vein and flows proximally through the needle 106 into the flash chamber 122. The flash chamber 122 can be sealed at one end by a flash plug 124.

The flash plug 124 can be made out of an air permeable, hydrophilic material that enables the passage of air, but inhibits the passage of liquid. For example, in one embodiment, the flash plug 124 can include a plurality of pores shaped and sized to enable the passage of low-pressure gas, but inhibit the passage of low-pressure liquid, such that the pores of the flash plug 124 become effectively sealed upon contact with the low-pressure liquid. Air that resides in the needle lumen and flash chamber 122 is therefore pushed through the flash plug 124 by the incoming blood, until the blood reaches the flash plug 124 or is otherwise stopped. In some embodiments, the needle hub 108, or portions thereof, can be constructed of a clear or translucent material configured to enable a clinician to view the presence of blood within the flash chamber 122. In this respect, the clinician can be alerted when the needle has entered the vein of the subject by the presence of blood within the flash chamber 122.

In one embodiment, features of the safety catheter insertion device 102, other than a flash chamber 122, can provide an indication that the sharp distal tip 118 has entered the vein of a subject. For example, the needle cannula 106 can include a notch 126. In this embodiment, blood flow enters the needle lumen when the sharpened distal tip 118 enters the vein. As blood flows proximately in the needle lumen, some blood passes through the notch 126 and into an annular space that lies between an exterior of the needle 106 and an interior of the catheter assembly 104. The presence of blood in the annular space can be viewed by a clinician through a clear or translucent portion of the catheter assembly 104, thereby providing an indication that the sharpened distal tip 118 is present in a vein.

The catheter assembly 104 can include a catheter hub 128 and a catheter tube 130. In one embodiment, the catheter tube 130 can extend from a tapered distal end to a proximal end, where the catheter tube 130 can be operably coupled to the catheter hub 128. The catheter tube 130 can define a lumen configured to provide a fluid pathway between a vein of a subject and the catheter hub 128. In one embodiment, the catheter tube 130 can include a barium radio opaque line to ease in the identification of the catheter tube 130 during radiology procedures. In some embodiments, the catheter tube 130 can include a necked-down portion 132 configured to provide a o-stage visual indication during catheter insertion into a vein of a patient. One example of a necked-down portion on a catheter tube 130 is disclosed in U.S. Provisional App. No. 62/575,045 (filed Oct. 20, 2017), the contents of which are incorporated by reference herein.

The catheter hub 128 can include a catheter hub body having a distal end, a proximal end and an internal wall defining an interior cavity therebetween. The interior cavity can include a proximal portion extending from the open proximal end, and a distal portion in closer proximity to the distal end. In one embodiment, the distal end of the catheter hub body is operably coupled to the proximal end of the catheter tube 130, such that the lumen of the catheter tube 130 is in fluid communication with the proximal portion of the interior cavity. In some embodiments, the proximal portion of the interior cavity can be shaped according to luer taper standards, so as to matingly receive a luer taper. The proximal end of the catheter hub body can also be provided with external ears, or the like, to secure the luer taper in the catheter hub 128, such as when the luer taper is coupled with a male luer lock collar of an administration set or syringe.

In some embodiments, the catheter assembly 104 can comprise a closed system catheter assembly. In one embodiment, the closed system catheter assembly 104 can further include an extension tube 134, an extension tube clamp 136, and a needleless connector 138. Some embodiments can further include a wing assembly and/or vent cap (not depicted). One such example of a closed system catheter assembly 104 is disclosed in U.S. Patent Publ. No. 2017/0239443, the contents of which are incorporated by reference herein.

Figure 2:
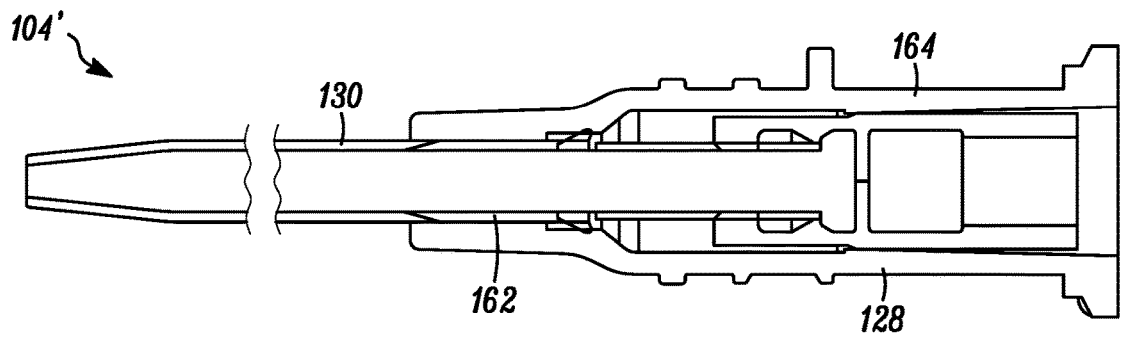
FIG. 2 is a partial, cross-sectional view depicting a safety catheter insertion assembly including a blood control feature, in accordance with an embodiment of the disclosure.

In one embodiment, the catheter assembly 104 can further include a blood control feature configured to inhibit blood from escaping after withdrawal of the needle cannula 106, thereby reducing the risk of exposure of blood or other bodily fluids to clinicians, particularly a consideration of sensitivity where blood-borne diseases may be present. Referring to FIG. 2, a partial cross sectional view of a catheter assembly 104' including a blood control feature is depicted in accordance with an embodiment of the disclosure. In one embodiment, the catheter assembly 104' can include an actuator 162 secured to the distal end of the catheter hub 128, so as to extend axially within the interior cavity. In one embodiment, the proximal end of the catheter tube 130 can be secured within the interior cavity of the catheter hub 128 with the aid of the actuator 162.

A seal member 164, alternatively referred to as a blood control valve, can also be secured within the interior cavity of the catheter hub 128 with the aid of the actuator 162, such that the seal member 164 is axially shiftable relative to the actuator 162 between a closed or sealed position in which flow of bodily fluid from the catheter tube 130 into the interior cavity of the catheter hub 128 is inhibited or restricted, and an open or actuated position, in which the seal member 164 is shifted relative to the actuator 162 thereby enabling the flow of bodily fluid from the catheter tube 130 into a proximal portion of the interior cavity of the catheter hub 128. Thus, the actuator 162 functions to both secure the catheter tube 130 to the catheter hub 128, and to support the seal member 164. One example of such a blood control feature is disclosed in U.S. Pat. No. 9,545,495, the contents of which are incorporated by reference herein.

Figure 3:
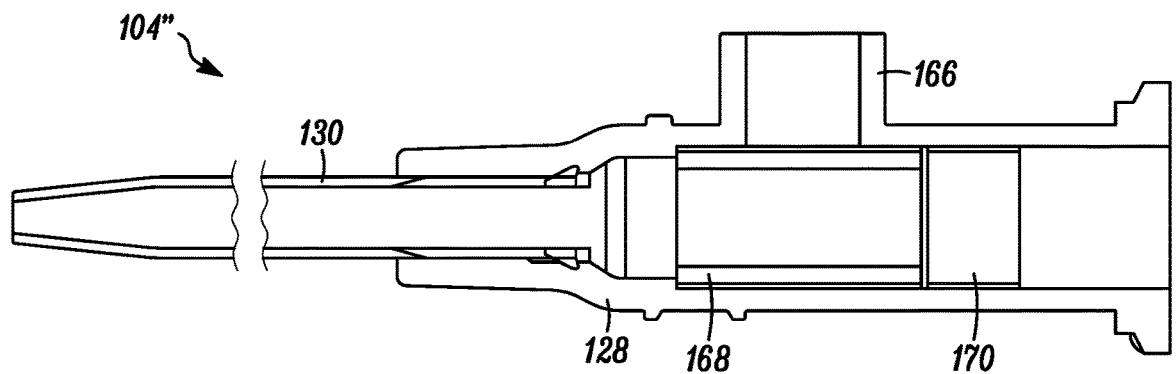
FIG. 3 is a partial, cross-sectional view of a safety catheter insertion assembly including a side port, in accordance with an embodiment of the disclosure.

In some embodiments, the catheter assembly 104 can include a side port. Referring to FIG. 3, a partial cross sectional view of a catheter assembly 104" including a side port 166 is depicted in accordance with an embodiment of the disclosure. In one embodiment, the interior wall of the catheter hub 128 can define a side port aperture 166 configured to enable an alternative fluid communication path with the interior cavity of the catheter hub 128. In one embodiment, the side port 166 can be positioned substantially orthogonal to a longitudinal axis of the catheter hub 128.

The side port 166 can be selectively sealed by a flexible sealing membrane 168 positioned within the interior cavity of the catheter hub 128. The sealing membrane 168 can be configured to deform when a sufficient fluid pressure is applied to the side port 166 from outside of the catheter hub 128, thereby enabling a flow of fluid into the interior cavity of the catheter hub 128. A septum or valve 170 can be positioned proximal to the sealing member 168 to inhibit fluid entering the interior cavity of the catheter hub 128 from the side port 166 from escaping out of the proximal end of the catheter hub 128. An example of such a septum or valve 170 is disclosed in U.S. Patent Publ. No. 2017/0239443, the contents of which are incorporated by reference herein.

Figure 4:
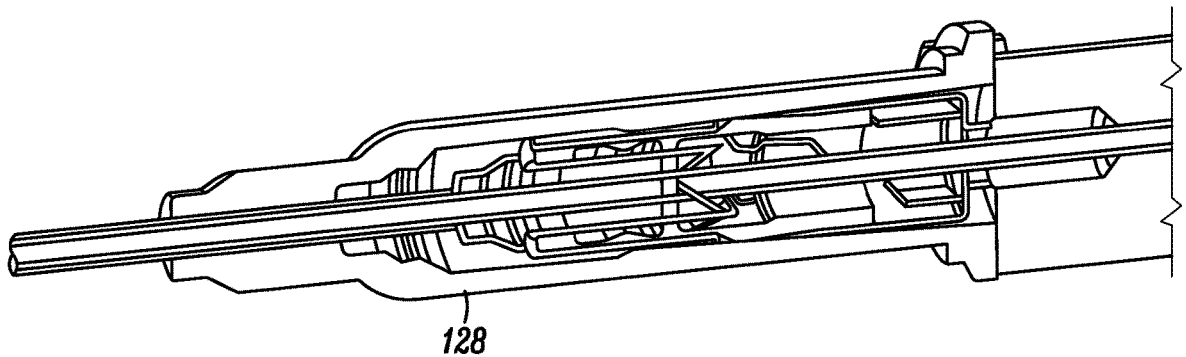
FIG. 4 is a partial, cross-sectional view of a safety catheter insertion assembly including an extended catheter hub, in accordance with an embodiment of the disclosure.

To ease in the interconnectability of the catheter assembly 104 to infusion tubing, the overall length of the catheter hub 128 can be increased. For example, as depicted in FIG. 4, the relative length of the catheter hub 128 along a longitudinal axis of the catheter hub 128 can be extended. For example, in one embodiment, the catheter hub 128 can measure between one and 2 inches in length.

Figure 5A:
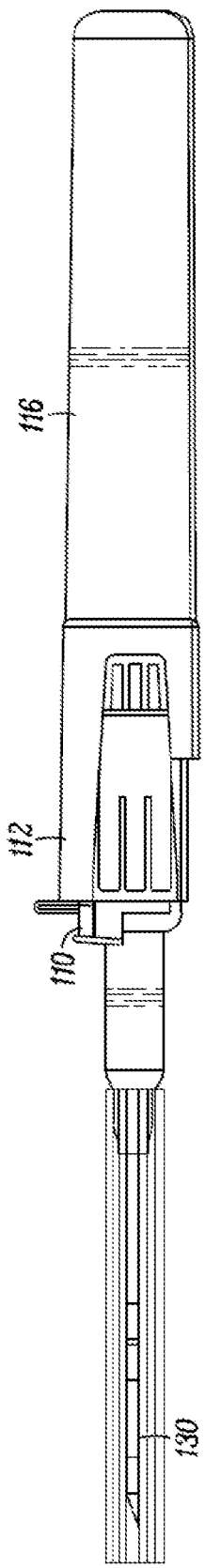
FIG. 5A is a profile view depicting an intravenous catheter assembly in accordance with an embodiment of the disclosure.
Figure 5B:
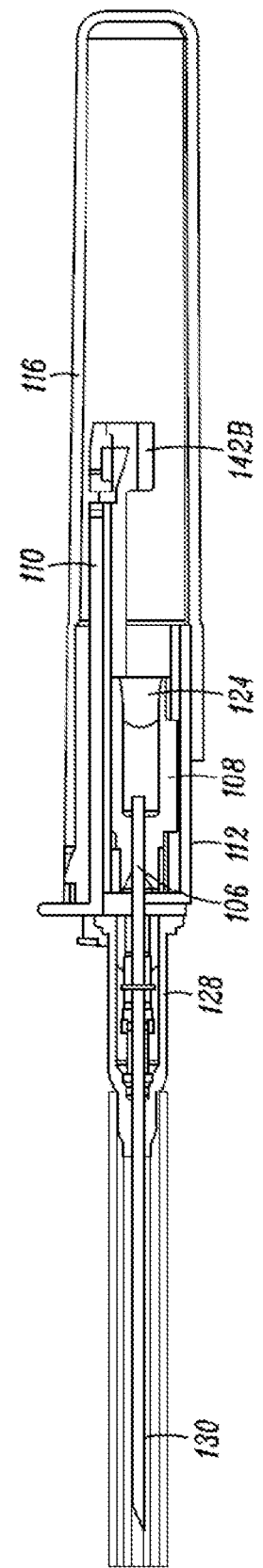
FIG. 5B is a cross-sectional view depicting the intravenous catheter assembly of FIG. 5A.

Referring to FIG. 5A, a profile view of an intravenous catheter insertion assembly 100 is depicted in accordance with an embodiment of the disclosure. FIG. 5B depicts a cross-sectional view of the intravenous catheter insertion assembly 100 of FIG. 5A. In one embodiment, the needle cannula 106 and needle hub 108 can be slidably coupled to the handle 112. The biasing mechanism 114 can be operably mounted between the needle hub 108 and the handle 112 to bias the needle hub 108 proximately away from the handle 112. In one embodiment the biasing mechanism 114 can be a compression spring. In one embodiment, one or more tabs 140A/B located on the needle hub 108 can be configured to interlock with a corresponding one or more retention arms located internally to the handle 112, so as to selectively retain the needle hub in close proximity to the handle 112 against the bias of the biasing mechanism 114.

The advancement arm 110 can be slidably coupled to the handle 112. In one embodiment, the advancement arm 110 can include one or more tabs 142A/B configured to interact with the one or more retention arms located internal to the handle 112. As discussed in greater detail below, sliding the advancement arm 110 distally relative to the handle 112 can enable the one or more tabs 142A/B to release of the interlock between the one or more tabs 140A/B located on the needle hub 108 and the one or more retention arms located internally to the handle 112, thereby enabling the bias of the biasing mechanism 114 to shift the needle hub 108 proximately away from the handle 112.

The needle housing 116 can be operably coupled to the handle 112. For example, in one embodiment, an exterior portion of the handle 112 can be shaped and sized to be matingly received within a proximal portion of the needle housing 116. In some embodiments, the handle 112 and the needle housing 116 can be fixedly coupled together, via a snaplock feature 150 (as depicted in FIG. 8B), interference fit, adhesive, ultrasonic welding, or the like. In one embodiment, the needle housing 116 and handle 112 can be collectively referred to as a needle housing assembly. As the needle hub 108 retracts under the bias of the biasing mechanism 114 away from the handle 112, at least a portion of the needle cannula 106 can be housed within the needle housing assembly.

As depicted in FIG. 6A, the intravenous catheter insertion assembly 100 can be provided in the first or ready for use position, in which the catheter assembly is connected to the safety catheter insertion device 102. In particular, the catheter tube 130, can be positioned over the needle cannula 106 of the safety catheter insertion device 102, with a sharp distal tip 110 of the needle 106 protruding from the distal end of the catheter tube 130. In some embodiments, the intravenous catheter insertion assembly 100 can be provided for use in a sterilized and assembled state, contained within a sealed package.

To insert the catheter into the vein of a subject, a clinician first removes the intravenous catheter insertion assembly 100 from the packaging. A needle sheath 144 covering the needle cannula 106 can be removed to expose the sharp distal tip 110 of the needle cannula 106. The clinician then punctures an identified site on the patient or subject with the sharp distal tip 110 and urges the needle cannula 106 forward until the sharp distal tip 110 and a portion of the catheter tube 130 enters the vein of the subject.

The advancement arm 110 can then be distally advanced relative to the handle 112, which forces the catheter assembly 104 to be moved distally over the needle 106, thereby threading the catheter assembly 104 into the vein of the subject as the handle 112 and needle housing 116 are held stationary.

As depicted in FIG. 6B, distal advancement of the advancement arm 110 eventually causes the protective needle cannula transposable mechanism to automatically withdraw the needle cannula 106 from the patient vein into a second or safe position, thereby inhibiting access to the sharp distal tip 118 of the needle cannula 106 for the purpose of inhibiting inadvertent needle sticks. Automatic withdrawal of the needle cannula 106 further enables release of the catheter hub 128 from the advancement arm 110. In the safe position, the clinician can dispose of the safety catheter insertion device 102 in a sharps container.

Figure 7A:
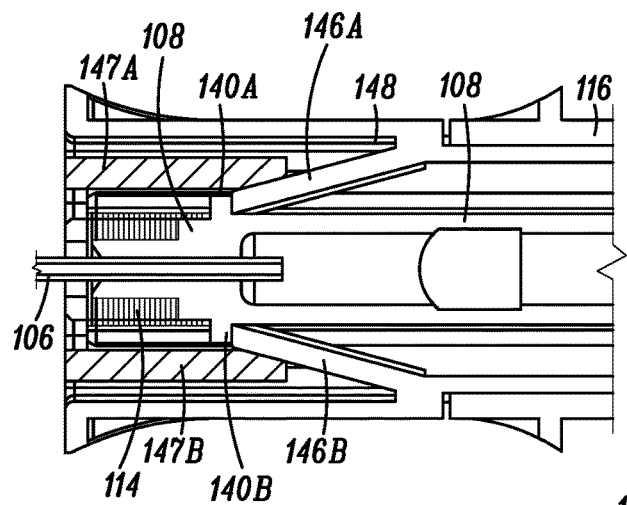
FIGS. 7A-D are partial, cross-sectional views depicting a safety catheter insertion device in various stages of operation, as an advancement arm is shifted distally relative to a handle, in accordance with an embodiment of the disclosure.
Figures 10A, 10B:
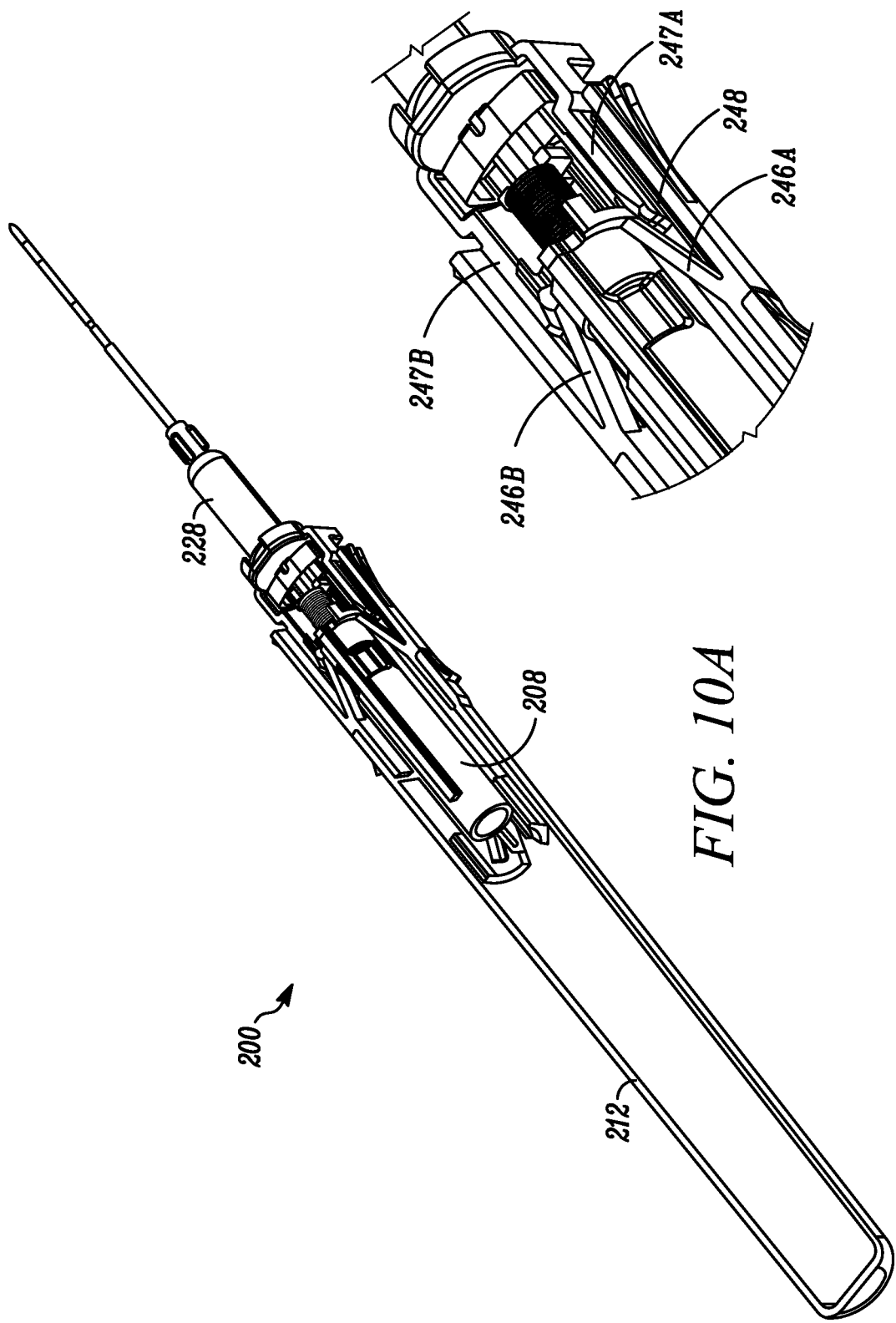
FIG. 10A is a perspective, cross-sectional view depicting the intravenous catheter assembly of FIG. 9A.
FIG. 10B is a close-up view of a portion of FIG. 10A depicting a pair of ribs of an advancement arm configured to inhibit premature release of the needle hub from a first or ready for use position.

Referring to FIGS. 7A-D, partial cross sectional views of the safety catheter insertion device in various stages of operation, as the advancement arm 110 is shifted distally relative to the handle 112, are depicted in accordance with an embodiment of the disclosure. In the first or ready for use position (as depicted in FIG. 7A), one or more tabs 140A/B of the needle hub 108 can be configured to engage with a corresponding one or more retention arms 146A/B located internal to the handle 112. In one embodiment, a pair of tabs 140A/B positioned on opposing sides of an outer diameter of the needle hub 108 can engage with a corresponding pair of retention arms 146A/B defined by the handle 112. In one embodiment, the retention arms 146A/B, which can angle outwardly from an interior surface 148 of the handle 112, can be constructed of a resilient material, thereby enabling the retention arms 146A/B to flex relative to the interior surface 148. In one embodiment, the retention arms 146A/B can be naturally biased away from the interior surface 148 at a predefined angle, so as to maintain the appropriate distance from the interior surface 148 to enable contact with the tabs 140A/B of the needle hub 108. In this manner, the retention arms 146A/B are configured to selectively lock the needle hub 108 in a distal position against the bias of the biasing mechanism 114, such that the sharp distal tip 118 of the needle cannula 106 protrudes from the distal end of the catheter tube 130 (as depicted in FIG. 6A). In one embodiment, premature movement of the retention arms 146A/B can be inhibited by the inclusion of one or more ribs 147A/B on the advancement arm 110. For example, in the first or ready for use position, the one or more ribs 147A/B can be positioned at least partially between the retention arms 146 and the interior surface 148 of the handle 112, thereby inhibiting deflection of the retention arms 146 and subsequent release of the needle hub 108 from the first or ready for use position. Another embodiment of an intravenous catheter insertion assembly 200 including one or more tabs 247A/B is depicted in FIG. 10A-B. like the previous embodiment, the one or more tabs 247A/B can inhibit premature release of the needle hub 208 from the first or ready for use position by being positioned between the retention arms 246A/B and the interior surface 248 of the handle 212, so as to inhibit unintended deflection of the retention arms 246A/B.

Figure 7B:
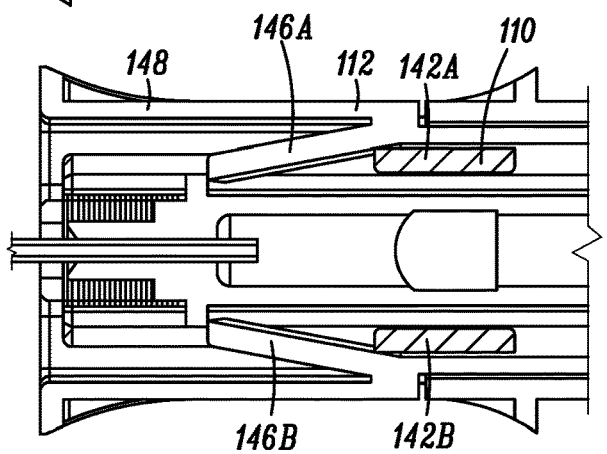
Figure 7C:
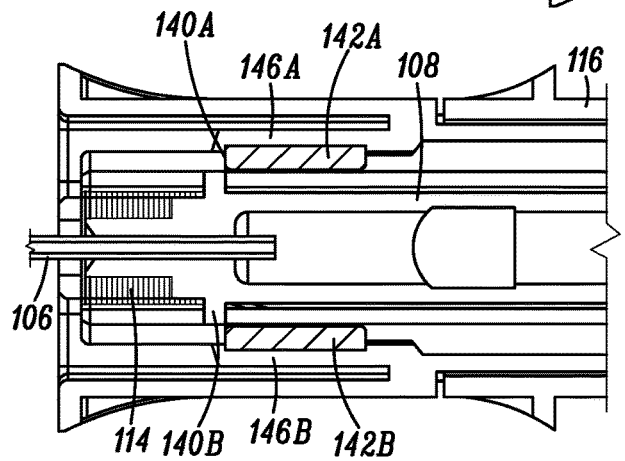

As depicted in FIGS. 7B and 7C, as the advancement arm 110 is shifted distally relative to the handle 112, the ribs 147A/B shift distally and the tabs 140A/B interact with the retention arms 146A/B to bend the retention arms 146A/B against their natural bias and towards the interior surface 148 of the handle 112. As the advancement arm 110 continues to be shifted distally, eventually the retention arms 146A/B of the handle 112 are moved out of interfering contact with the tabs 140A/B of the needle hub 108. Removal of the interfering contact between the retention arms 146A/B and the tabs 140A/B enables the biasing mechanism 114 to naturally bias the needle hub 108 proximally away from the handle 112, thereby shifting the needle cannula 106 proximally out of the catheter tube 130 and into the needle housing 116.

Figure 7D:
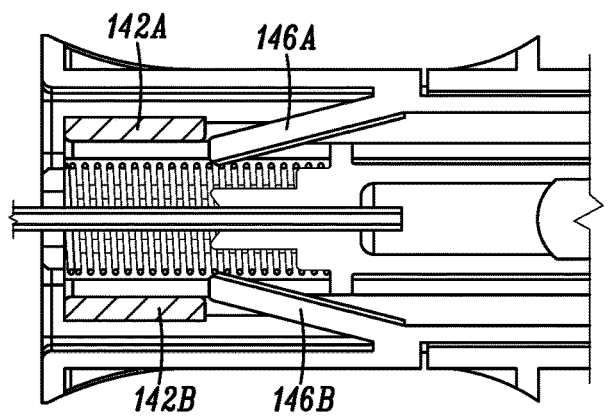

Referring to FIG. 7D, in some embodiments, further distal advancement of the advancement arm 110 can cause the tabs 142A/B of the advancement arm 110 to shift distally beyond the retention arms 146A/B. Thereafter, the retention arms 146A/B can resume their natural unbiased configuration away from the interior surface 148 at the predefined angle, thereby inhibiting proximal movement of the tabs 142A/B back to the first or ready for use position. In other embodiments, the advancement arm 110 can be shifted proximally relative to the handle 112 after release of the needle hub 108.

Figure 8A:
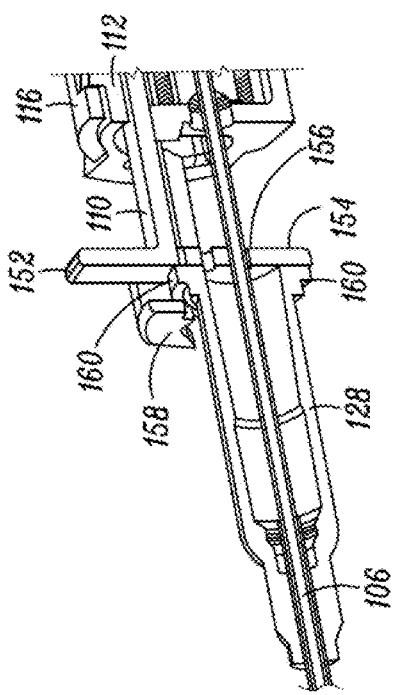
FIG. 8A is a partial, cross-sectional view depicting an intravenous catheter insertion assembly in which a catheter hub is constrained relative to an advancement arm by the passage of the needle cannula therethrough, in accordance with an embodiment of the disclosure.
Figure 8B:
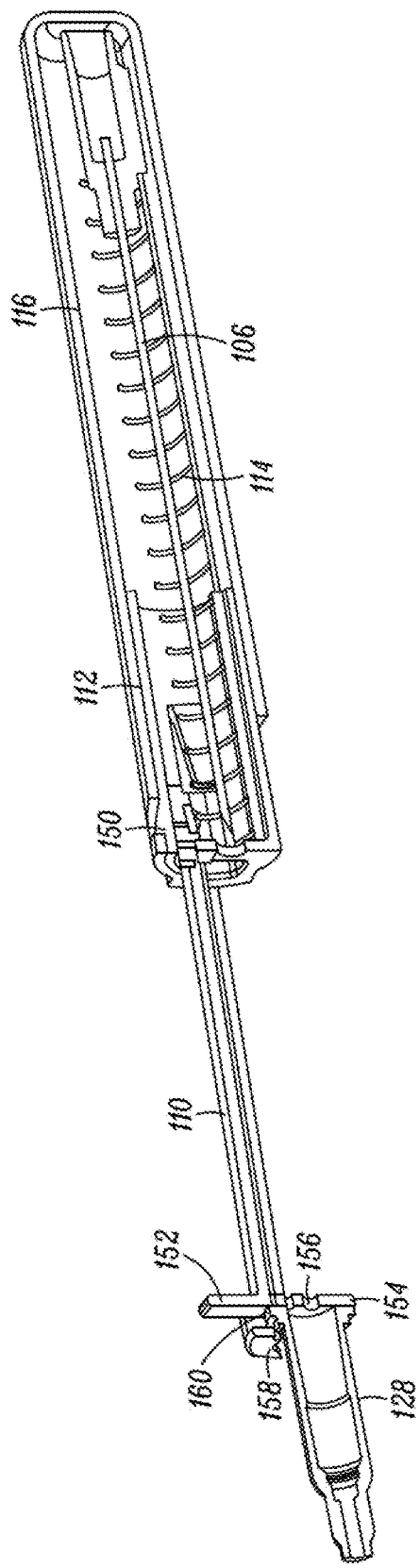
FIG. 8B is a partial, cross-sectional view depicting the intravenous catheter insertion assembly of FIG. 8A, in which the needle cannula has been retracted and the restraint of the catheter hub relative to the advancement arm has been removed, in accordance with an embodiment of the disclosure.

Referring to FIG. 8A, a partial cross sectional view of an intravenous catheter insertion assembly 100, in which the catheter hub 128 is constrained relative to the advancement arm 110 by the passage of the needle cannula 106 therethrough, is depicted in accordance with an embodiment of the disclosure. Referring to FIG. 8B, a cross-sectional view of the intravenous catheter assembly 100 of FIG. 8A, in which the needle cannula 106 has been retracted and the constraint of the catheter hub 128 relative to the advancement arm 110 has been removed, is depicted in accordance with an embodiment of the disclosure.

In one embodiment, the advancement arm can include a distal end catheter hub coupling portion 152. The catheter hub coupling portion 152 can include an abutment plate 154 configured to selectively abut up against the proximal end of the catheter hub 128, when the catheter assembly 104 is operably coupled to the safety catheter insertion device 102. The abutment plate 154 can include an aperture 156 configured to enable the needle cannula 106 to pass therethrough.

Structure defining a hub grip 158 can extend distally from the abutment plate 154. The hub grip 158 can be shaped and sized to closely conform to an outer diameter of the catheter hub 128 distal to an extending ridge or external ears 160 of the catheter hub 128. The hub grip 158 can be distally spaced apart from the abutment plate 154 at a distance sized to closely conform to a width of the extending ridge or external ears 160. Accordingly, in the first or ready for use position, the catheter assembly 104 can be operably coupled to the safety catheter insertion device 102 by the proximal end of the catheter hub 128 abutting up against the abutment plate 154, the extending ridge or external ears 160 of the catheter hub 128 positioned between the abutment plate 154 and the hub grip 158, and the outer diameter of the catheter hub 128 abutting up against a portion of the hub grip 158.

In some embodiments, release of the catheter hub 128 from the catheter hub coupling portion 152 can be affected by shifting the advancement arm 110 upward and away from the catheter hub 128, thereby causing the extending ridge or external ears 160 to move out from between the abutment plate 154 and the hub grip 158, and removing abutment of the outer diameter of the catheter hub 128 from the hub grip 158. Further shifting of the advancement arm 110 relative to the catheter hub 128 can remove abutment of the proximal end of the catheter hub 128 from the abutment plate 154, thereby causing the safety catheter insertion device 102 to separate from the catheter assembly 104.

In the first or ready for use position, passage of the needle cannula 106 through the catheter hub coupling portion 152 and the catheter hub 128 can restrain the advancement arm 110 from shifting upwardly and away from the catheter hub 128, thereby inhibiting separation of the safety catheter insertion device 102 from the catheter assembly 104. In some embodiments, the aperture 156 of the abutment plate 154 can be shaped and sized to closely conform to an outer diameter of the needle cannula 106, thereby minimizing the degree to which the advancement arm 110 is able to shift relative to the catheter hub 128 when the needle cannula 106 passes therethrough.

Accordingly, the catheter hub coupling portion 152 can function as a passive release mechanism. The term passive release mechanism, as used herein, as understood to refer to features of a intravenous catheter insertion assembly 100 that inhibit the release of the catheter assembly 104 from the safety catheter insertion device 102 until after the sharp distal tip 110 of the needle cannula 106 has been housed within the needle housing assembly. Some or all of the features of the passive release mechanism can be integral with other components of the catheter insertion assembly 100. In this respect, the term passive release mechanism does not necessarily refer to a component that is separate from the safety catheter insertion device 102 and/or the catheter assembly 104. Rather, it is to be appreciated that various components of the safety catheter insertion device 102 and/or catheter assembly 104 can form the passive release mechanism.

In one embodiment, the passive release mechanism can be configured to couple the catheter hub 128 to the safety catheter insertion device 102 in the first or ready for use position, and release the catheter hub 128 from the safety catheter insertion device 102 in the second or safe position. Further, the passive release mechanism inhibits release of the catheter hub 128 from the safety catheter insertion device 102 until after the sharp distal tip 110 of the needle cannula 106 is in a safe position, where access to the sharp distal tip 110 is inhibited. Release of the catheter hub 128 from the safety catheter insertion device 102 can occur during a catheter insertion procedure without a need to perform additional steps. In this respect, the catheter can be "passively" released by a clinician to obtain passive safety. By way of example, the catheter can be released when a clinician pulls on a portion of the safety catheter insertion device 102 as the clinician inserts and positions the catheter assembly 104.

Referring to FIG. 9A, a perspective view of an alternative embodiment of an intravenous catheter insertion assembly 200 is depicted in accordance with the disclosure. FIG. 9B depicts an exploded view of the intravenous catheter insertion assembly 200 of FIG. 9A. FIG. 10A depicts a perspective, cross-sectional view of the intravenous catheter insertion assembly 200 of FIG. 9A. FIG. 10B depicts a close-up view of a portion of the intravenous catheter insertion assembly 200 of FIG. 10A. The intravenous catheter insertion assembly 200 can be similar to previously disclosed embodiments, with the further inclusion of a hub retention clip 262, configured to inhibit removal of the catheter assembly 204 from the safety catheter insertion device 202 prior to withdrawal of the needle cannula 206.

As depicted, the intravenous catheter insertion assembly 200 can include a safety catheter insertion device 202 and a catheter assembly 204. The safety catheter insertion device 202 can include a needle cannula 206, needle hub 208, advancement arm 210, handle 212, compression spring 214, and needle housing 216. The catheter assembly 204, like previously disclosed embodiments, can include a catheter hub 228 and a catheter tube 230. A needle sheath 244 can be optionally coupled to the catheter assembly 204 prior to use.

Figure 11B:
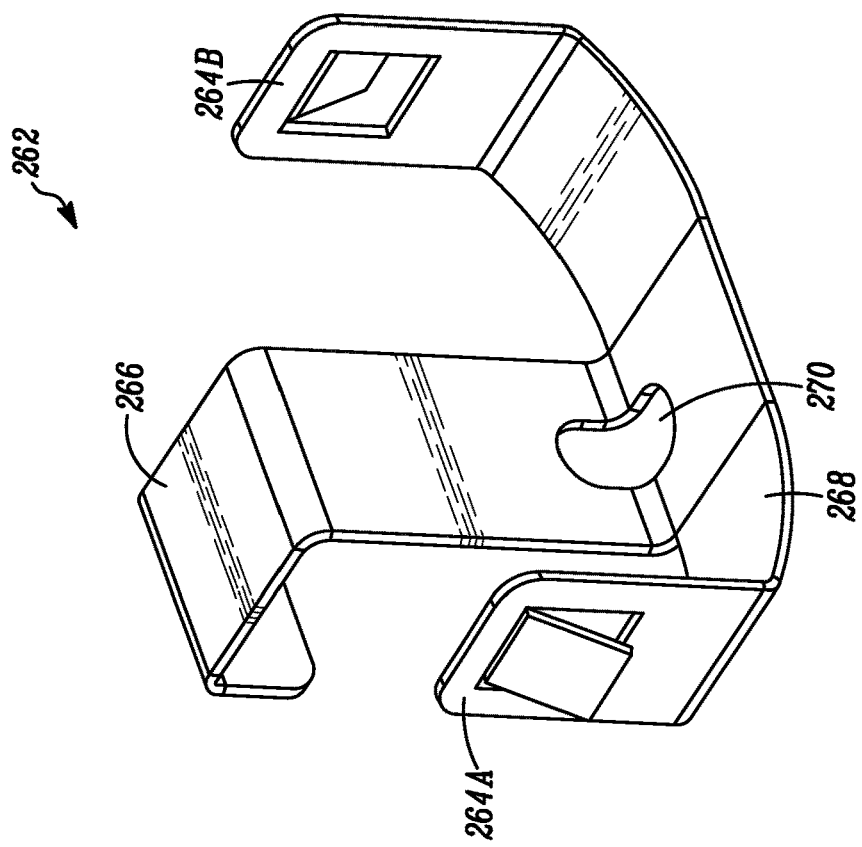
FIG. 11A-B are close-up, perspective views depicting a hub retention clip, in accordance with an embodiment of the disclosure.
Figure 11A:
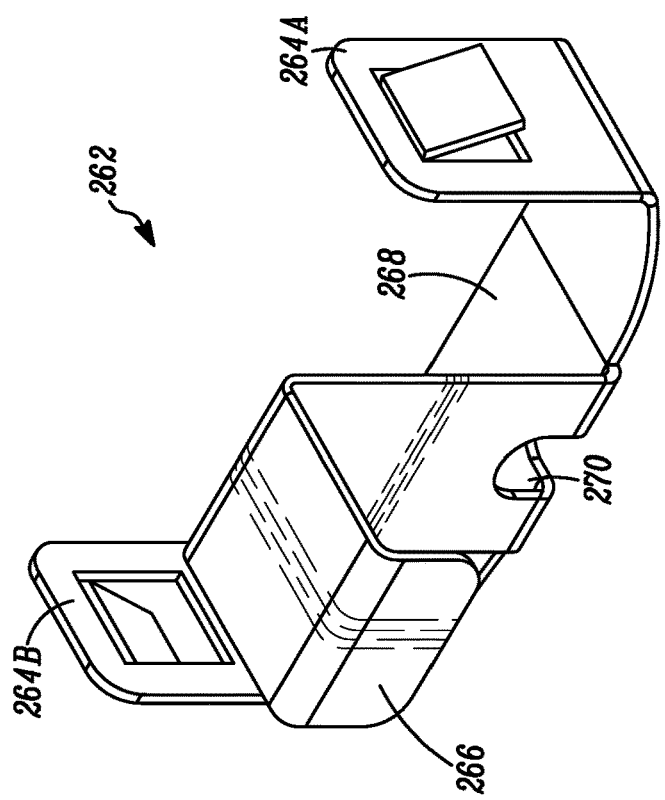

Referring to FIG. 11A-B, close-up perspective views of a hub retention clip 262 are depicted in accordance with an embodiment of the disclosure. The hub retention clip 262 can include one or more anchor portions 264A/B, catheter hub retention portion 266, and bridge portion 268. The one or more anchor portions 264A/B can be configured to operably coupled to the advancement arm 210. In one embodiment, at least the bridge portion 268 of the hub retention clip 262 can be constructed of a resilient material. The catheter hub retention portion 266 can be configured to conform to an outer diameter and extending ridge or external ears 260 of a catheter hub 228. For example, in one embodiment, the catheter hub retention portion 266 can be comprised of a thin web of metal or the like, and can be formed in a "U" configuration shaped and sized to closely conform to the outer diameter and extending ridge or external ears 260 of a catheter hub 228. In one embodiment, at least one of the catheter hub retention portion 266 and/or bridge portion 268 can define an aperture 270 configured to enable a portion of the needle cannula 204 to pass therethrough.

Figure 12A:
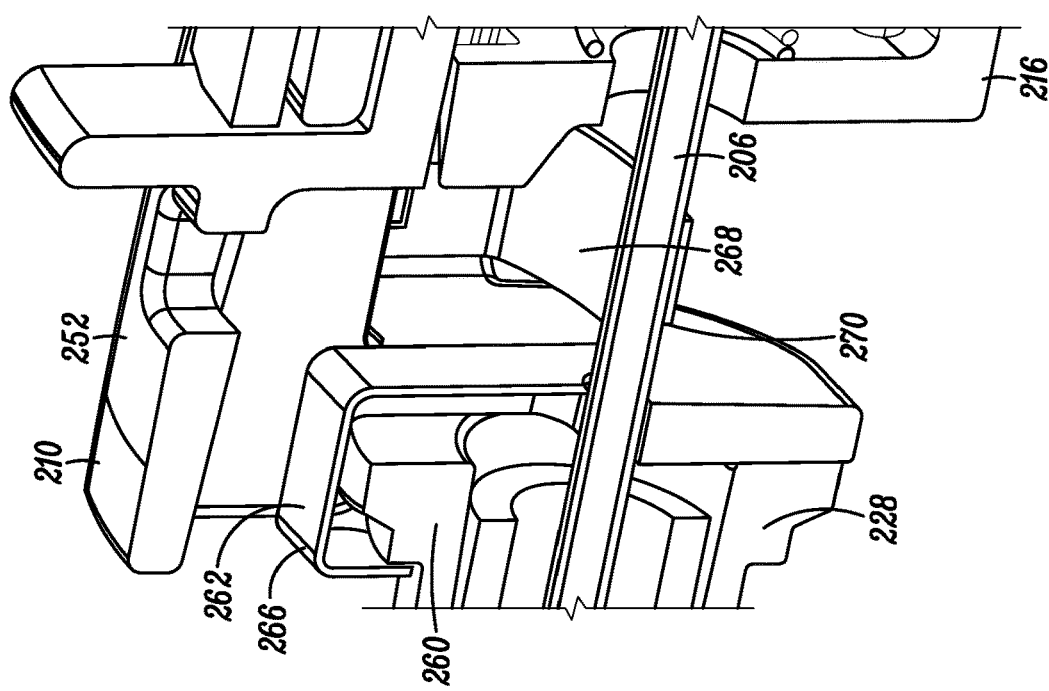
FIG. 12A is a partial perspective, cross-sectional view depicting an intravenous catheter insertion assembly, in which a hub retention clip operably couples a catheter hub to a catheter insertion device.
Figure 13B:
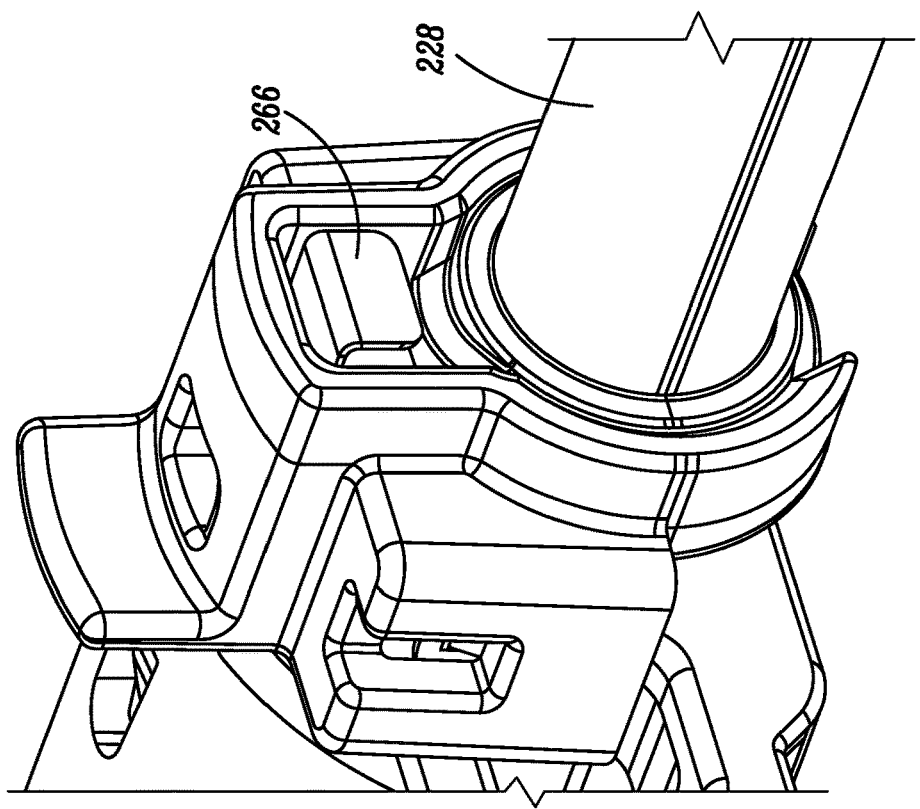
FIG. 13B is a partial perspective view depicting the intravenous catheter insertion assembly of FIG. 13A, in which the hub retention clip is shifted away from the catheter hub, thereby releasing the catheter hub from the catheter insertion device.
Figure 13A:
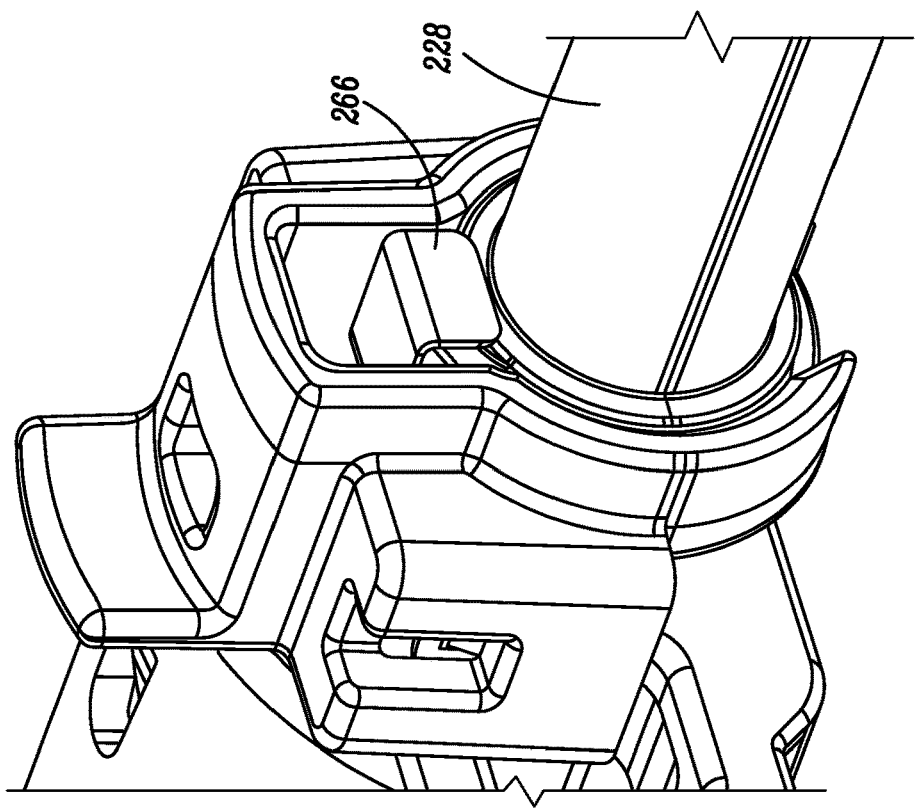
FIG. 13A is a partial perspective view depicting an intravenous catheter insertion assembly, in which a hub retention clip operably couples a catheter hub to a catheter insertion device.

In some embodiments, a distal end of the advancement arm 210 and the hub retention clip 262 can form a catheter hub coupling portion 252. As depicted in FIG. 12A, the hub retention clip 262 can be configured to operably couple a catheter hub 228 to the catheter insertion device 202. In particular, the hub retention clip 262 can be configured to inhibit release of the catheter hub 228 prior to proximal withdrawal of the needle cannula 206 into the needle housing 216. For example, in one embodiment, the passage of the needle cannula 206 through the aperture 270 of the hub retention clip 262 can retain the hub retention clip 262 in a first or ready for use position, in which the bridge portion 268 of the hub retention clip 262 is flexed away from the advancement arm 110 against its natural bias. In this position, the catheter hub retention portion 266 can maintain contact with the outer diameter and extending ridge or external ears 260 of a catheter hub 228. FIG. 13A depicts a partial perspective view of the catheter hub retention portion 266 in contact with the catheter hub 228. Accordingly, in the first or ready for use position, passage of the needle cannula 206 through the aperture 270 of the hub retention clip 262 and the catheter hub 228 can inhibit removal of the catheter assembly 104 from the safety catheter insertion device.

Figure 12B:
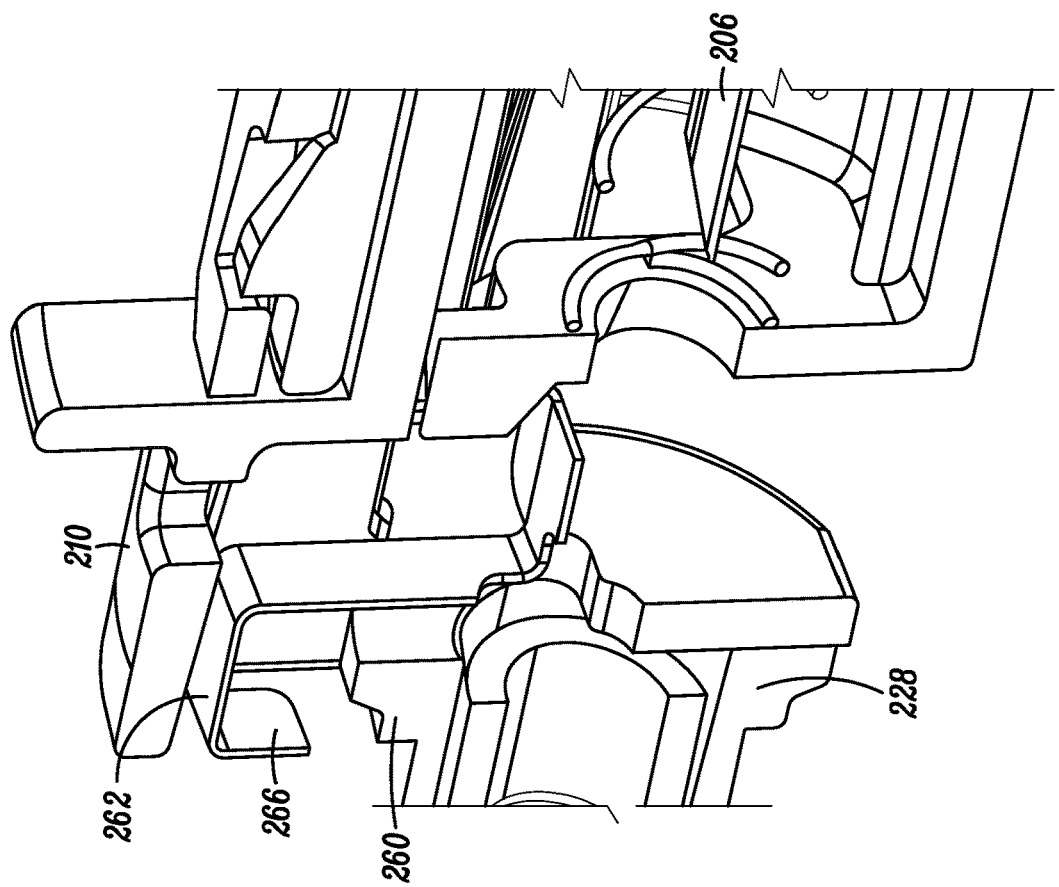
FIG. 12B is a partial perspective, cross-sectional view depicting the intravenous catheter insertion assembly of FIG. 12A, in which the hub retention clip is shifted away from the catheter hub, thereby releasing the catheter hub from the catheter insertion device.

As depicted in FIG. 12B, when the needle cannula 206 is proximally withdrawn within the needle housing 216, the hub retention clip 262 shifts relative to the advancement arm 210, thereby releasing the catheter hub 128. In particular, withdrawal of the needle cannula 206 proximally beyond the bridge portion 268 of the hub retention clip 262 enables the bridge portion 268 of the hub retention clip 262 to resume its natural, unbiased shape, thereby shifting the catheter hub retention portion 266 away from the outer diameter and extending ridge or external ears 260 of a catheter hub 228. FIG. 13B depicts a partial perspective view of the catheter hub retention portion 266 shifted away from the catheter hub 228. Thereafter, the catheter assembly 204 can be separated from the safety catheter insertion device 202. Accordingly, the hub retention clip 262 and advancement arm 210 can collectively function as a passive release mechanism.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

The invention claimed is:

1. A safety catheter insertion device configured to automatically retract a needle cannula following insertion of a catheter assembly and to inhibit release of the catheter assembly from the safety catheter insertion device until the needle cannula has been automatically retracted for the purpose of inhibiting inadvertent needle sticks, the safety catheter insertion device comprising:
 a needle assembly including a needle cannula having a sharpened distal tip and a proximal end operably coupled to a needle hub;
 a needle housing assembly configured to selectively house the sharpened distal tip of the needle assembly in a proximal position, the needle housing assembly defining one or more retention arms extending at an angle outwardly from an interior surface of the needle housing assembly, the one or more retention arms constructed of a resilient material naturally biased away from the interior surface of the needle housing assembly;
 a spring mechanism positioned between the needle hub and the needle housing and configured to bias the needle assembly to the proximal position; and
 an advancement arm slidably coupled to the needle housing and configured to shift between a first position in which a portion of the needle cannula traverses through a catheter hub coupling portion of the advancement arm to inhibit release of a catheter assembly from the safety catheter insertion device, and a second position in which one or more tabs of the advancement arm flex the one or more retention arms of the needle housing assembly relative to the interior surface of the needle housing assembly to enable the spring mechanism to shift the needle assembly to the proximal position to house the sharpened distal tip of the needle assembly in the needle housing assembly and enable release of the catheter assembly from the safety catheter insertion device, wherein in the first position one or more ribs of the advancement arm contact the one or more retention arms of the needle housing assembly to inhibit premature movement of the one or more retention arms relative to the interior surface of the needle housing assembly.

2. The safety catheter insertion device of claim 1, wherein the needle hub includes one or more tabs, wherein the one or more tabs interlock with the one or more retention arms of the needle housing assembly to retain the needle assembly in a distal position against the bias of the spring mechanism.

3. The safety catheter insertion device of claim 2, wherein the one or more retention arms of the needle housing assembly are biased towards engagement with the one or more tabs of the needle hub.

4. The safety catheter insertion device of claim 3, wherein the one or more tabs of the advancement arm shift the one or more retention arms of the needle housing assembly against their natural bias away from engagement with the one or more tabs of the needle hub.

5. The safety catheter insertion device of claim 1, wherein in the second position, interaction between the one or more retention arms of the needle housing assembly and the one or more tabs of the advancement arm inhibit further shifting of the advancement arm relative to the needle housing assembly.

6. The safety catheter insertion device of claim 1, wherein the spring mechanism is a compression spring.

7. The safety catheter insertion device of claim 1, wherein the catheter hub coupling portion of the advancement arm includes an abutment plate and hub grip shaped and sized to closely conform to an outer diameter of a catheter hub of the catheter assembly.

8. The safety catheter insertion device of claim 1, wherein the catheter hub coupling portion of the advancement arm includes a hub retention clip.

9. The safety catheter insertion device of claim 8, wherein contact between the hub retention clip and a catheter hub of the catheter assembly is maintained by the passage of the needle cannula through a portion of the hub retention clip.

10. The safety catheter insertion device of claim 9, wherein withdrawal of the needle cannula to the proximal position enables a natural bias of the hub retention clip to shift the hub retention clip away from the catheter hub.

11. A safety catheter insertion device configured to inhibit release of a catheter assembly from the safety catheter insertion device until a needle cannula has been automatically retracted into a needle housing for the purpose of inhibiting inadvertent needle sticks, the safety catheter insertion device comprising:
  a needle assembly including a needle cannula having a sharpened distal tip and a proximal end operably coupled to a needle hub;
  a needle housing assembly configured to selectively house the sharpened distal tip of the needle assembly in a proximal position, the needle housing assembly including one or more retention arms constructed of a resilient material and extending at an angle outwardly from an interior surface of the needle housing assembly;
  a spring mechanism positioned between the needle hub and the needle housing and configured to bias the needle assembly to the proximal position;
  an advancement arm slidably coupled to the needle housing assembly; and
  a hub retention clip operably coupled to a distal portion of the advancement arm,
  wherein the advancement arm is configured to slide between a first position in which a portion of the needle cannula traverses through the hub retention clip to inhibit release of the catheter assembly from the safety catheter insertion device, and a second position in which the needle cannula is retracted under the bias of the spring mechanism to the proximal position to house the sharpened distal tip of the needle assembly in the needle housing assembly and enable release of the catheter assembly from the safety catheter insertion device, wherein in the first position one or more ribs of the advancement arm contact the one or more retention arms of the needle housing assembly to inhibit premature movement of the one or more retention arms relative to the interior surface of the needle housing assembly.

12. The safety catheter insertion device of claim 11, wherein withdrawal of the needle cannula to the proximal position enables a natural bias of the hub retention clip to shift the hub retention clip away from the catheter hub.

13. The safety catheter insertion device of claim 11, wherein one or more tabs of the needle hub interlock with one or more retention arms of the needle housing assembly to retain the needle assembly in a distal position against the bias of the spring mechanism.

14. The safety catheter insertion device of claim 13, wherein the one or more retention arms of the needle housing assembly are biased towards engagement with the one or more tabs of the needle hub.

15. The safety catheter insertion device of claim 14, wherein one or more tabs of the advancement arm shift the one or more retention arms of the needle housing assembly against their natural bias away from engagement with the one or more tabs of the needle hub.

* * * * *